United States Patent [19]

Josephson

[11] 4,267,272

[45] May 12, 1981

[54] PROSTATIC ACID PHOSPHATASE IMMUNO ASSAY

[75] Inventor: Lee Josephson, Arlington, Mass.

[73] Assignee: Baxter Travenol Laboratories, Inc., Deerfield, Ill.

[21] Appl. No.: 91,622

[22] Filed: Nov. 5, 1979

[51] Int. Cl.³ .............................................. C12Q 1/66
[52] U.S. Cl. ...................................... 435/7; 435/21; 435/188; 435/196
[58] Field of Search ..................... 435/7, 195, 196, 21, 435/188

[56] References Cited
PUBLICATIONS

Andras G. Foti, et al., Clinical Chemistry, vol. 23, No. 1, pp. 95–99, 1977.

*Primary Examiner*—Robert J. Warden
*Attorney, Agent, or Firm*—Paul C. Flattery; Lawrence W. Flynn; Max D. Hensley

[57] ABSTRACT

Prostatic acid phosphatase is immunologically unstable under typical laboratory conditions. Thus it is necessary to combine a stabilizing composition with samples taken for immunological assay of prostatic acid phosphatase content, and to similarly stabilize prostatic acid phosphatase-containing reagents in kits used to assay the enzyme.

8 Claims, 1 Drawing Figure

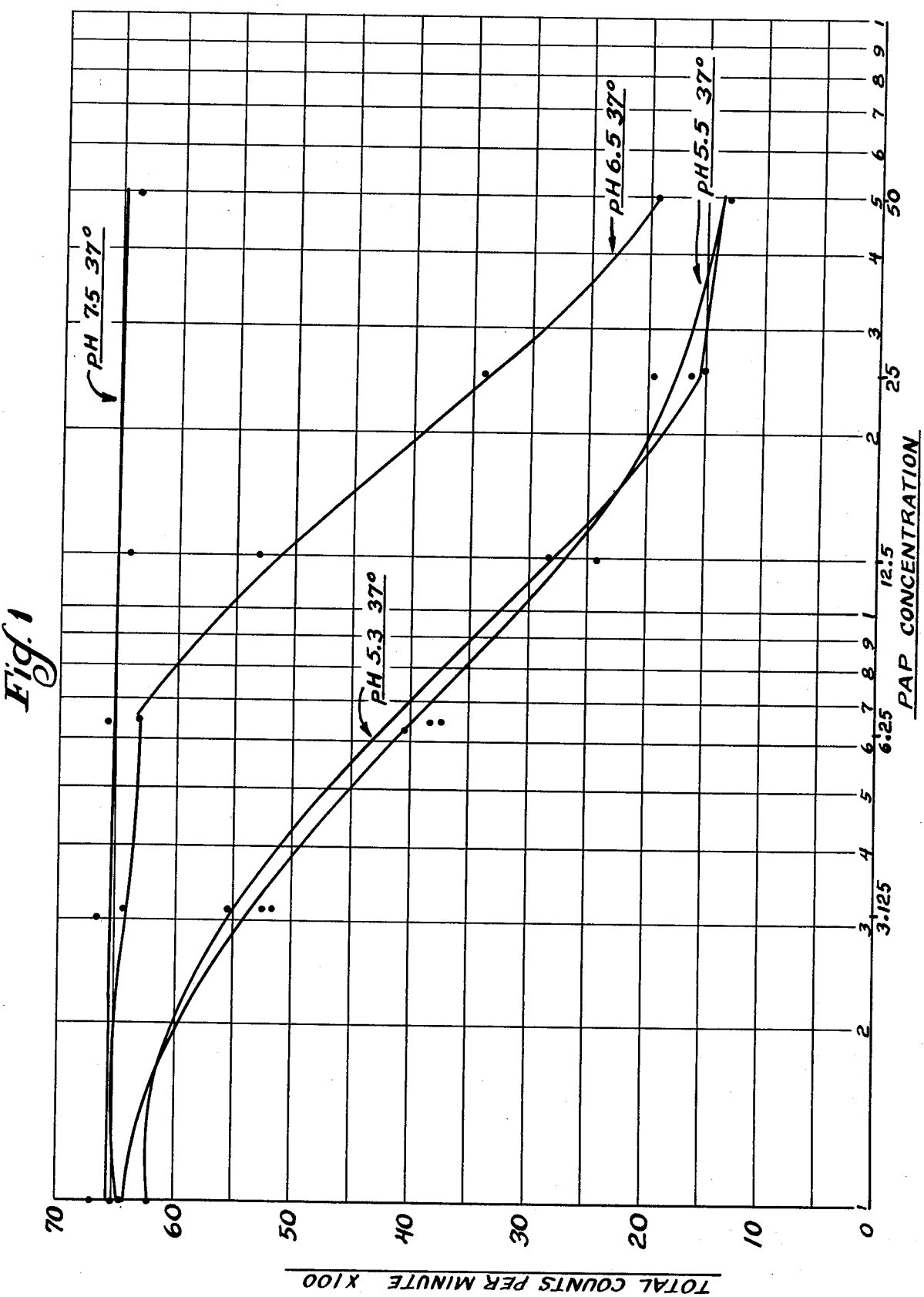

PROSTATIC ACID PHOSPHATASE IMMUNO ASSAY

This invention relates to specific binding assays for enzymes. In particular this invention relates to the accurate immunological determination of prostatic acid phosphatase.

BACKGROUND OF THE INVENTION

Specific binding methods for the determination of enzymes have become firmly established. These methods are to be distinguished from methods where the catalytic activity of an enzyme is followed by measuring the action of the enzyme on its substrate, either by disappearance of the substrate or appearance of a product. Specific binding methods use no enzyme substrate, but instead employ a binding partner for the enzyme which is capable of reversibly, noncovalently binding the enzyme. Antibodies are oridinarily used as such binding partners because they are simple to make and handle. However, other binding partners such as cell surface receptors or carrier proteins may be useful.

Specific binding methods for the determination of enzymes may employ any of the routine procedures used previously for specific binding assays of non-enzyme antigens. For example, the well known sandwich or competitive immunoassays, as well as the homogeneous or heterogeneous enzyme-linked immunoassays, may be used. Such methods are routinely practiced in clinical laboratories using commercial kits containing all the reagents necessary to conduct the assay, e.g. labelled sample analogue, binding substance and standards. In the case of competitive immunoassays, however, it is preferred to insolubilize the antibody-bound enzyme after the sample and tracer enzyme have competed for limited antibody sites in solution. Insolubilization is conventionally accomplished by precipitating the immune complex of antibody and enzyme with a second antibody directed against the enzyme-binding antibody.

All of the labels heretofore used in specific binding assays may be employed for the determination of enzymes. Radioisotopes, stable free radicals, fluorescent and chemiluminescent compounds, enzymes, and coenzymes are all satisfactory, although enzyme and coenzyme labels should be selected to minimize interference from the enzyme of interest or enzymes in the sample to be determined.

Prostatic acid phosphatase (PAP) is now routinely determined by immunoassay. PAP (orthophosphoric monoester phosphohydrolase, acid optimum, E. C. 3.1.3.2) is a glycoprotein of approximately 100,000 daltons molecular weight. It is a major constituent of seminal fluid, normally secreted into semen and urine, and is present in serum at low levels. The acid phosphatases in general are distributed widely in the human body, and were first identified in human erythrocytes. They are present primarily in platelets, but also found in other blood cell components and maturing cells in the bone marrow as well as the epithelial cells and secretions of the prostate gland. The serum acid phosphatase level is normally a mixture of the enzymes contributed by the various tissue cells.

Discovery several decades ago that serum acid phosphatase activity is elevated in metastatic cancer of the prostate led to spectrophotometric assays for PAP activity which follow the enzymatic, or catalytic activity of PAP. Drawbacks to these assays are numerous. For example, lack of specificity for PAP is only partially overcome by the use of differential substrates and inhibitors. The major limitation is that these methods have generally been useful only for detection of metastatic prostatic cancer, and do not show adequate sensitivity for detection of the more curable earlier stages.

PAP immunoassays have been an improvement over the previous enzyme assays. They are more specific for the prostatic isoenzyme and exhibit greater sensitivity than the earlier enzyme assays, thus reportedly aiding in the more reliable detection of premetastatic prostatic cancer. Thus, excellent quantitation of serum PAP has been made practical by the use of immunoassay.

One advantage that has been urged in support of immunological rather than enzymatic methods for determining PAP is that the enzyme is immunologically stable, even though enzymatic acitivity may be rapidly lost. Thus no special steps have been used to preserve the PAP activity of samples as measured by enzyme assay. Foti et al., "Clinical Chemistry" 23 (1):9599 (1977), disclose that PAP is enzymatically unstable at 23° C., for only about 25% of the starting PAP activity can be detected by an enzymatic assay, after sample storage for 48 hours at 23° C. The enzyme instability notwithstanding, according to Foti et al. the conventional PAP determination by radioimmunoassay will produce constant PAP values.

Foti et al. do disclose some immunological activity losses at 37° C. However, since assays generally wil be conducted at room temperature, i.e., close to 23° C., Foti et al. concluded that "serum samples do not require special treatment (e.g., pH adjusting) and handling" before the PAP assay is conducted. Incidently, the pH adjustment mentioned by Foti et al. is a conventional step used in the earlier enzymatic assays for PAP: It has been considered good practice to acidify samples prior to PAP enzymatic assays because the enzyme activity is preserved at low pH.

Foti et al. also disclose the use of L-tartrate in enzymatic PAP assays. L-tartrate is a specific inhibitor for PAP which has the advantage that it does not appreciably inhibit other phosphatases. This phenomenon has been employed in PAP enzyme assays by first determining the total phosphatase activity of the sample and then the sample activity in the presence of L-tartrate. The difference between the two determinations is taken as the PAP activity. Foti et al. disclose that L-tartrate and other PAP inhibitors such as oxalate or fluoride do not interfere in the PAP immunoassay.

The conclusion of Foti et al. that PAP enzymatic activity is irrelevant to PAP immunoassay has been generally embraced by the art, but not without some confusion. For example, Endocrine Sciences' direction insert for its PAP radioimmunoassay unequivocally states that "detection of prostatic acid phosphatase by RIA is not dependent upon retention of enzyme activity in the serum sample", yet later observes that "PAP stability is decreased at room temperature . . . values were found to be somewhat lower after two days . . . samples for PAP analysis, therefore, should not be left at ambient temperatures for prolonged periods." Regardless of whether or not previous workers have recognized the immune instability of PAP, the concensus appears to be that enzyme stabilizers such as acid should not be added to the samples, standards or controls to be used in PAP immunoassays. Representative of this belief is Wang Laboratory's admonishment in its PAP radioimmunoassay direction insert that "(sample) sera should not contain any additive or acidifying agent." Similarly, while the New England Nuclear PAP RIA direction insert provides for reconstitution of lyophilized PAP tracer in pH 5.1 buffer (at which PAP is stable), it specifies a pH 7.4 buffer for reconstitution of the PAP standards.

Surprisingly, it has been found that the previously held beliefs of the prior art regarding PAP immunological stability have been incorrect. PAP is immunologically recognized by antibodies elucidated by the enzymatically active enzyme only for so long as it remains in the enzymatically active form. In fact, the decay of immunological activity closely parallels enzyme activity decay. The result of this misconception is that immunoassays currently being sold are capable of detecting only about 50% to 80% of the enzymatically inactive form of PAP. It is likely that serum samples will lose PAP enzyme activity at a different rate than PAP standards because of differences in collection and processing. Where such a discrepancy exists, the resulting assays will yield incorrect PAP values. For example, since standards heretofore generally have been supplied lyophilized and since the prior art instructions have been to include no additives or acid stabilizers in test samples, it is probable that the loss of PAP immunological activity in samples has exceeded that in standards. An assay conducted under these circumstances will yield artifically low PAP values. Even if by chance the standards and samples had suffered the identical degree of PAP inactivation at the time of assay, the resultant lower effective analyte concentration for both standards and sample would reduce the overall assay snesitivity. These unfortunate results neutralize the principal advantages espoused for PAP immunoassay: Reliable and sensitive PAP detection. The Endocrine Sciences' suggestion that PAP samples not be permitted to remain at ambient temperatures for prolonged periods, i.e., two days, is not adequate to fully protect the integrity of the assay because unacceptable losses in PAP immunological activity occur during this period.

OBJECTS OF THE INVENTION

Thus it is a foremost object of this invention to provide a specific binding assay procedure for PAP which will accurately measure the enzyme.

It is a further object of this invention to provide stable PAP standards for use in specific binding methods for PAP.

SUMMARY OF THE INVENTION

Once the problem of PAP immunological instability is recognized, steps must be taken to preserve the immunological activity in samples and standards. Accordingly, the objects of the invention are accomplished in a specific binding assay for PAP by contacting PAP samples and standards with a stablizing composition for the immunological activity of PAP. More specifically, since it is now recognized that immunological activity parallels enzyme activity, the objects of the invention are achieved in a specific binding assay for PAP by contacting PAP samples and standards with a stabilizing composition previously employed to stabilize PAP enzyme activity.

BRIEF DESCRIPTION OF THE DRAWING

FIG. 1 illustrates the deleterious effects on the immune stability of PAP when PAP samples are stored at 37° C. in the absence of stabilizer, in accordance with previous practice. This FIGURE also shows that reducing the pH to stabilize the enzyme activity of PAP, contrary to the suggestions of the prior art, also immunologically stabilizes the enzyme.

DESCRIPTION OF THE PREFERRED EMBODIMENTS

The composition to be used to stabilize PAP depends upon the specific binding protein, normally an antibody, which is to be used in the assay. Generally, the stabilizer should prevent any changes in PAP from one immunologically distinct species to another. This means that the immunological features of PAP in samples, standards and tracer not be permitted to change relative to one another. For example, PAP antibodies are usually elicited by immunizing a suitable animal against the enzymatically active form of PAP. With such antibodies it is necessary to prevent the degradation or transformation of enzymatically active PAP into a moiety which is not bindable by the antibody, i.e. to prevent losses in immunological activity, for such losses in immunological activity have been found to correlate with losses in enzymatic acitivity. Hence, where an assay employs antibody directed against enzymatically active PAP the stabilizer should be capable of stabilizing the enzyme activity of PAP. However, stabilizing the enzymatic activity of PAP to preserve its immunological activity is but one embodiment of this invention.

PAP enzymatic activity may be stabilized by any of the compositions heretofore used to stabilize PAP in enzyme assays for PAP. Acids have been commonly used for this purpose. Test samples are collected into and standards prepared in an acidic medium, conventionally a buffer having a pH of from about 4.0 to about 6.5, preferably pH 5.0 to 5.5. Citrate and glutamate buffers are particularly useful. Alternatively, serum or plasma samples may be simply adjusted to the desired pH with an acid, either a mineral acid such as HCl or an organic acid such as acetic acid, without the use of an exogenous buffer.

Competitive inhibitors for PAP enzymatic activity such as L-tartrate and fluoride may be employed as stabilizers, but they are not as effective as acid in stabilizing the PAP immunological activity. Hence the preferred role of tartrate or fluoride is as a supplement to other stabilizers. Thus it is preferred to collect samples into and prepared standards in pH 5-5.5 phosphate buffer containing 1 mM L-tartrate.

An additional group of stabilizers are specific binding proteins for PAP, in particular PAP antibodies. Whether or not antibodies are used as stablizers depends upon balancing the comparative advantages and disadvantages of precombining antibody with standards and samples before the conduct of the assay. The benefits include a savings in laboratory time and reduction in laboratory error. The disadvantages include a requirement for a longer incubation period in competitive-type PAP immunoassays. On balance, specific binding proteins are not preferred for use as stabilizers.

The invention will be more fully understood by reference to the following examples.

EXAMPLE 1

PAP is determined using a competitive binding assay incorporating a precipitating antiserum reagent to separate antibody-bound tracer and antigen from the unbound tracer and antigen. In this method non-radioactive PAP from serum samples, PAP standards or PAP controls compete with a constant amount of radioiodinated PAP tracer [hereafter ($^{125}$I) PAP] for binding sites on the PAP antibody, which is held at a limiting concentration in relation to the total PAP and ($^{125}$I) PAP concentration. The amount of ($^{125}$I) PAP which will bind to the antibody is inversely proportional to the amount of non-radioactive PAP present in the assay tube.

The precipitating reagent solution, containing an antibody to PAP antibody is used to separate the antibody-bound ($^{125}$I) PAP from unbound ($^{125}$I) PAP by immunoprecipitation. After incubating the precipitating reagent with the reaction mixture the assay tubes are centrifuged and the supernatants are decanted. The antibody-bound ($^{125}$I) PAP, which is in the precipitate, is counted in a gamma counter. A standard curve is constructed and the PAP concentrations of the samples are interpolated from the standard curve.

Since the enzyme and immune activies of PAP are unstable it is recommended that samples be acidified as soon as possible after collection and that they be stored at 2° to 8° C. or frozen if lengthy storage, i.e., greater than 2 days, is anticipated.

The PAP assay was conducted at 20°–27° C. Plastic or glass test tubes were labelled in duplicate according to the scheme shown below in Table 2. The following reagents were added to the appropriate tubes in duplicate:

a. 100 microliters of PAP Serum Blank, 0 ng/ml, pH 5.5.

b. 100 microliters of each PAP Serum Standard, pH adjusted to 5.5 with acetic acid.

c. 100 microliters of PAP Control Serum 5.0 ng PAP/ml, pH adjusted to 5.5 with acetic acid.

d. 100 microliters of each sample.

Then 100 microliters of goat anti-PAP serum in pH 6.8 phosphate buffer containing bovine serum albumin and 0.003 M sodium azide were added to all tubes, mixed, and the composition incubated for 18 hours. ($^{125}$I) PAP was dissolved in pH 5.0 phosphate buffer containing 0.001 M tartrate. 100 microliters of this tracer solution were added to each tube and mixed; total counts-per-minute added were approximately 27,000. After 3 hours incubation 1.0 ml of horse anti-goat serum in phosphate buffer containing 0.02 M ethylenediaminetetracetic acid and 0.003 M sodium azide preservative was added to each tube and mixed. All tubes were incubated for 30 minutes and centrifuged for 20 minutes at a minimum relative centrifugal force of 1000 X g in a refrigerated centrifuge. The soluble contents of each tube were decanted and the precipitated residue counted for one minute in a gamma counter with the window suitably adjusted for iodine-125. The results are set forth in Table 2.

TABLE 2

| Tube No. | Contents of Tubes in ng/ml | CPM Bound | PAP Concentration (ng/ml) |
|---|---|---|---|
| 1 | PAP Serum Blank, 0 | 13,126 | — |
| 2 | " | 13,104 | — |
| 3 | PAP Serum Standard, 1.0 | 11,742 | — |
| 4 | " | 11,900 | — |
| 5 | PAP Serum Standard, 3.0 | 9,567 | — |
| 6 | " | 9,685 | — |
| 7 | PAP Serum Standard, 10.0 | 5,008 | — |

TABLE 2-continued

| Tube No. | Contents of Tubes in ng/ml | CPM Bound | PAP Concentration (ng/ml) |
|---|---|---|---|
| 8 | " | 5,161 | — |
| 9 | PAP Serum Standard, 30.0 | 2,548 | — |
| 10 | " | 2,736 | — |
| 11 | PAP Control Serum, 5.0 | 7,594 | 5.2 |
| 12 | " | 7,650 | 5.1 |
| | | | Av. 5.2 |
| 13 | Patient "X" Serum Sample | 7,286 | 5.6 |
| 14 | " | 7,478 | 5.3 |
| | | | Av. 5.5 |
| 15 | Patient "Y" Serum Sample | 3,275 | 20.2 |
| 16 | " | 3,250 | 20.5 |
| | | | Av. 20.4 |

EXAMPLE 2

This example demonstrates the lability of PAP when PAP is determined by immunoassay. Four series of PAP standard having 0, 3.125, 6.25, 12.5, 25 and 50 ng PAP/ml were prepared by adding the requisite amount of PAP to normal human serum containing sodium azide preservative and adjusting the pH to 5.3, 5.5, 6.5, or 7.5. The standards were incubated at 37° C. for 18 hours and assayed essentially by the method of Example 1, except that the incubation of PAP tracer, standards and anti-PAP was continued for 48 hours rather than 18 hours and 0.5 ml of rabbit anti-goat serum was employed. The ratio of (1) radio-activity bound by anti-PAP to (2) the total counts added was determined for each standard at each pH and plotted on semilogarithmic chart paper. The results are shown in FIG. 1. As can be seen from this FIGURE, PAP incubated at pH 7.5 and 37° C. is ineffective at any concentration in displacing tracer PAP from anti-PAP, thus indicating that the treated PAP has lost the capacity to be immunologically recognized by its antibody. On the other hand, PAP which was incubated under acidic conditions, i.e., pH 5.3 or 5.5, retained the capacity to compete with tracer PAP for antibody binding sites. Thus it is concluded that PAP is immunologically unstable within the pH range of normal serum but that the PAP inactivation can be prevented by the addition of a PAP stabilizing composition such as acid.

We claim:

1. In an immunoassay for PAP wherein the amount of PAP in PAP standards is determined, the improvement comprising contacting the standards with a composition for stabilizing the enzymatic activity of PAP under conditions that would otherwise render the standard PAP ineffective in displacing tracer PAP from PAP antibody thereby also stablizing the PAP immunological activity.

2. The method of claim 1 wherein the composition is an antibody to PAP.

3. The method of claim 1 wherein the composition is an acid.

4. In an immunoassay method for PAP, the improvement comprising PAP standards having a pH of about from 5.0 to 5.5.

5. The method of claim 4 wherein the PAP standard is at about pH 5.5.

6. The immunoassay method of claim 4 wherein the standard further contains an inhibitor of PAP enzyme activity.

7. The method of claim 6 wherein the inhibitor is L-tartrate.

8. The immunoassay method of claims 1 or 4 wherein the standard includes human serum.

* * * * *